United States Patent [19]

Ichikawa

[11] Patent Number: 4,969,875
[45] Date of Patent: Nov. 13, 1990

[54] DRAINAGE DEVICE FOR MEDICAL USE

[76] Inventor: Kazuo Ichikawa, 65-14, Okita, Wakabayashi Higashi-cho, Toyota-shi, Aichi-ken, Japan

[21] Appl. No.: 354,590

[22] Filed: May 22, 1989

[51] Int. Cl.⁵ .............................................. A61M 25/00
[52] U.S. Cl. .................................. 604/164; 604/158; 604/170
[58] Field of Search .............................. 604/158–170, 604/51; 128/657

[56] References Cited

U.S. PATENT DOCUMENTS

| Re. 31,855 | 3/1985 | Osborne | 604/161 |
|---|---|---|---|
| 4,166,469 | 9/1979 | Littleford | 604/164 |
| 4,230,123 | 10/1980 | Hawkins, Jr. | 604/165 |
| 4,351,333 | 9/1982 | Lazarus et al. | 604/164 |
| 4,405,314 | 9/1983 | Cope | 604/164 |
| 4,552,554 | 11/1985 | Gould et al. | 604/164 |
| 4,636,199 | 1/1987 | Victor | 604/164 |
| 4,650,472 | 3/1987 | Bates | 604/158 |
| 4,677,978 | 7/1987 | Melker | 604/51 |
| 4,687,469 | 8/1987 | Osypka | 604/161 |
| 4,705,041 | 11/1987 | Kim | 128/343 |
| 4,772,266 | 9/1988 | Groshong | 604/164 |
| 4,804,365 | 2/1989 | Litzie et al. | 604/170 |
| 4,813,929 | 3/1989 | Semrad | 604/164 |

FOREIGN PATENT DOCUMENTS 62-78938   5/1987   Japan .

Primary Examiner—Stephen C. Pellegrino
Assistant Examiner—Ralph Lewis
Attorney, Agent, or Firm—Armstrong, Nikaido, Marmelstein, Kubovcik & Murray

[57] ABSTRACT

A drainage device used in the body cavity comprising a flexible metallic guide wire capable of being inserted into a puncture needle, a tube-like dilator made of slightly hard synthetic resin and covering the outer periphery of the guide wire, a drainage tube made of synthetic resin in which a wire is embedded and covering the outer periphery of the guide wire, a sheath made of synthetic resin having a total length shorter than that of the dilator and having at a proximal portion of the sheath a fastening plug to be liquidtightly connected to a fastening jack of the dilator, and a universal fastening jack to be detachably attached to an end of the drainage tube and to be liquidtightly connected to the fastening plug.

The draingage device can simplify the insertion of the drainage tube and shorten the time required for manual drainage operation.

2 Claims, 6 Drawing Sheets

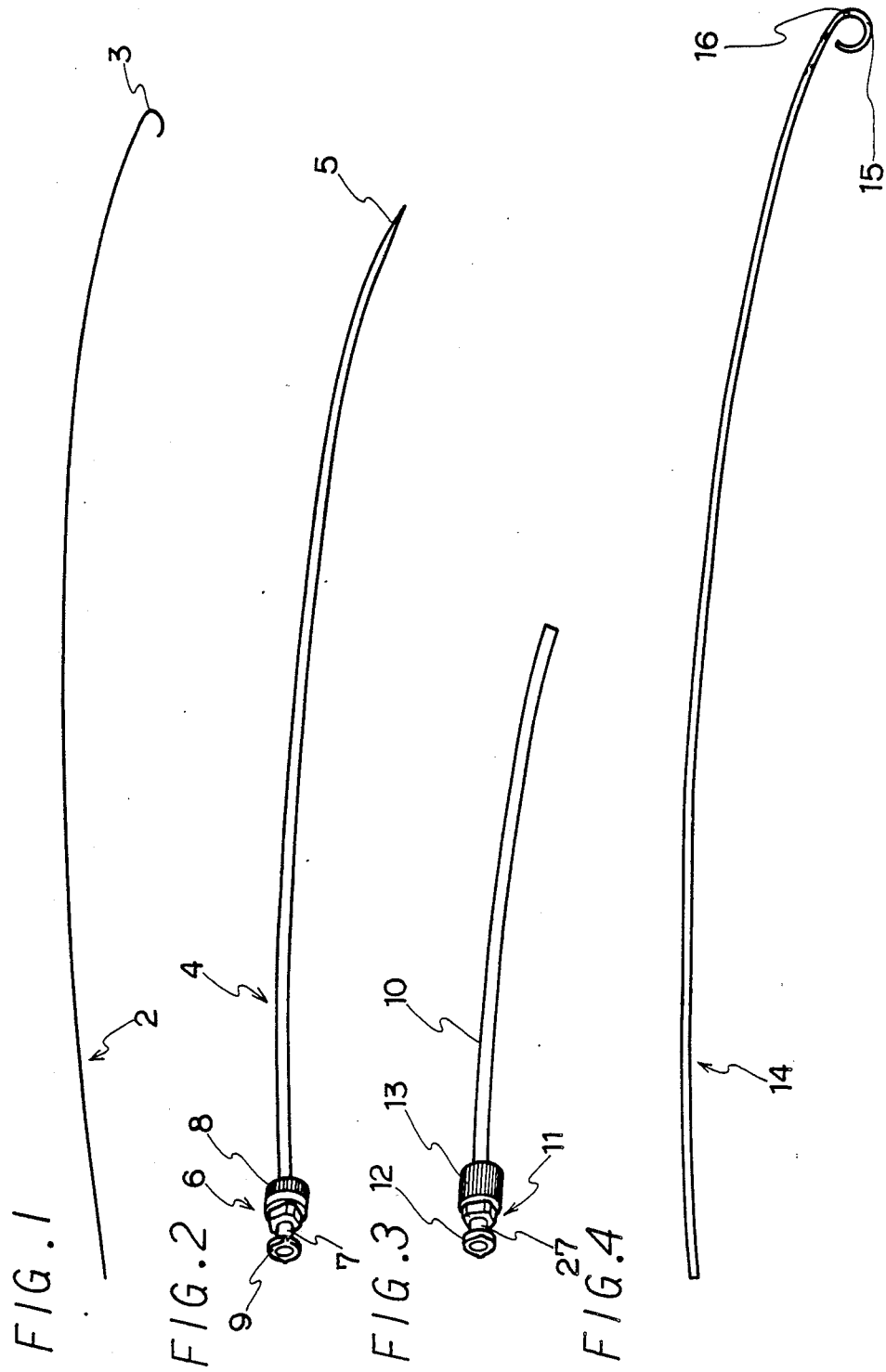

DRAINAGE DEVICE FOR MEDICAL USE

BACKGROUND OF THE INVENTION

The present invention relates to a drainage device used for body cavity drainage carried out in the examination or treatment of various kinds of cholangia sickness and the like.

In recent years, a percutaneous transphepatic cholangio-drainage (PTCD) has been widely used in diagnosis and treatment of cholangia sickness. With the wide use of PTCD, improvement of devices used therein and manual operation has been made, so that it has recently become customary to carry out drainage operation in which a puncture needle having a small diameter of 21G. (21 gauge: 0.813 mm OD) or 22G. (0.711 mm OD) is sticked and inserted into a bile duct through a right chest wall. Due to such drainage operation, the possibility of complication due to mannual operation has been reduced.

In the conventional method, however, there is the danger of the drainage tube bending in the abdominal cavity due to respiration or movement of a patient and dislodging from a bile duct. The dislodgement of the drainage tube in the abdominal cavity causes a very serious complication such as bile peritonitis. Such a situation becomes life threatening to the patient and requires an urgent drainage.

Further, there is a one step method such as a method wherein a thick puncture needle (for example 18G.: 1.219 mm OD) is initially sticked into the body cavity and a guide wire is inserted into the puncture needle, and then a large diameter dull needle on which a catheter is put is inserted into the body cavity along the guide wire after the puncture needle is pulled out by a conventional dull needle on which a catheter is put. However, in such a method operator of the dull needle sometimes feels a large resistance when inserting the dull needle since a tip of the dull needle has a dull taper (i.e., a tip of the dull needle is not to sharply pointed. Therefore, the above discussed one step method gives a great pain to a patient.

In the case of a two step method, (a thin puncture needle (for example 22G.) is initially sticked into the body cavity and a guide wire is inserted into the puncture needle, and then a dilation is gradually carried out by using two kinds of dull needles on which a catheter is put respectively, that is, by using a small diameter dull needle and a large diameter dull needle) by conventional dull needles. However, the two-step method becomes an operation which is time-consuming and complicated.

The present invention resolves the above-mentioned problems, and it is an object of the present invention to provide a drainage device capable of shortening the time required for inserting a drainage tube and preventing the drainage tube from dislodging from the bile duct.

SUMMARY OF THE INVENTION

In accordance with the present invention, there is provided a drainage device used in the body cavity comprising: a flexible metallic guide wire capable of being inserted into a puncture needle; a tube-like dilator made of slightly hard synthetic resin such as "Teflon" so as to be elastically bendable and covering an outer periphery of the guide wire, an outer diameter of a tip portion of the dilator being gradually reduced toward an end of the dilator to be taper-shaped, and the dilator having a fastening jack at a proximal portion of the dilator; a drainage tube made of synthetic resin in which a wire is embedded except at a curled elastic tip portion and covering the outer periphery of the guide wire, and having at least one hole at the tip portion; a sheath made of synthetic resin such as Teflon and having a total length shorter than that of the dilator, the sheath covering the outer periphery of the dilator and the drainage tube and having at a proximal portion of the sheath a fastening plug to be liquidtightly connected to the fastening jack; and a universal fastening jack to be detachably attached to an end of the drainage tube and to be liquidtightly connected to the fastening plug.

BRIEF EXPLANATION OF THE DRAWINGS

FIG. 1 is a perspective view of an embodiment of a guide wire in the present invention;

FIG. 2 is a perspective view of an embodiment of a dilator in the present invention;

FIG. 3 is a perspective view of an embodiment of a sheath in the present invention;

FIG. 4 is a perspective view of an embodiment of a drainage tube in the present invention;

DETAILED DESCRIPTION

Figure 8:
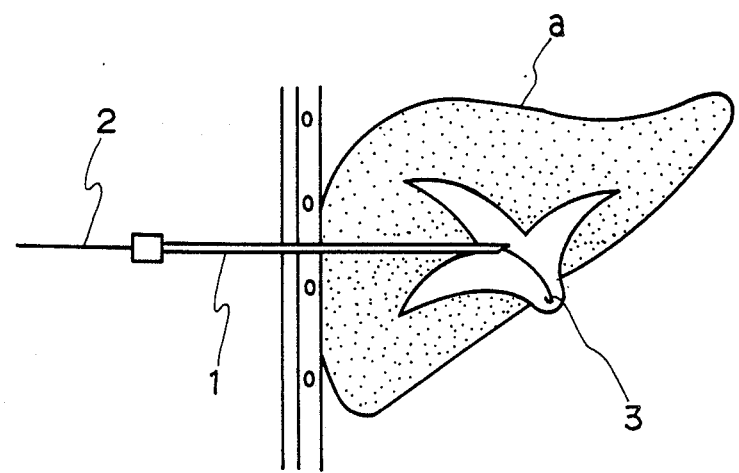
Figure 9:
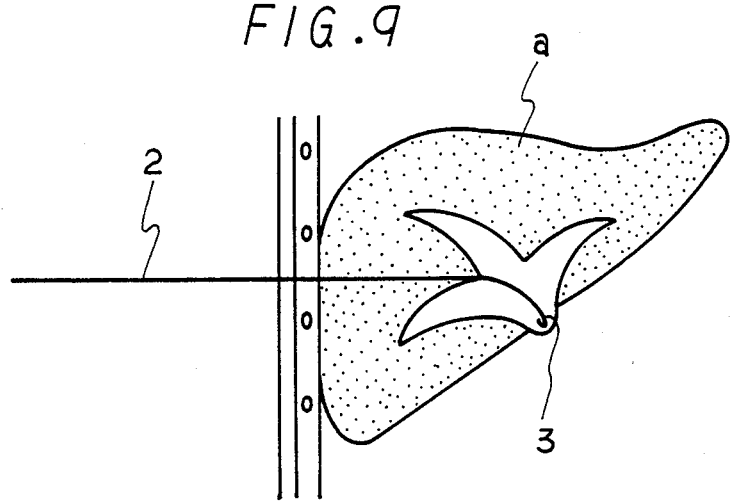
Figure 10:
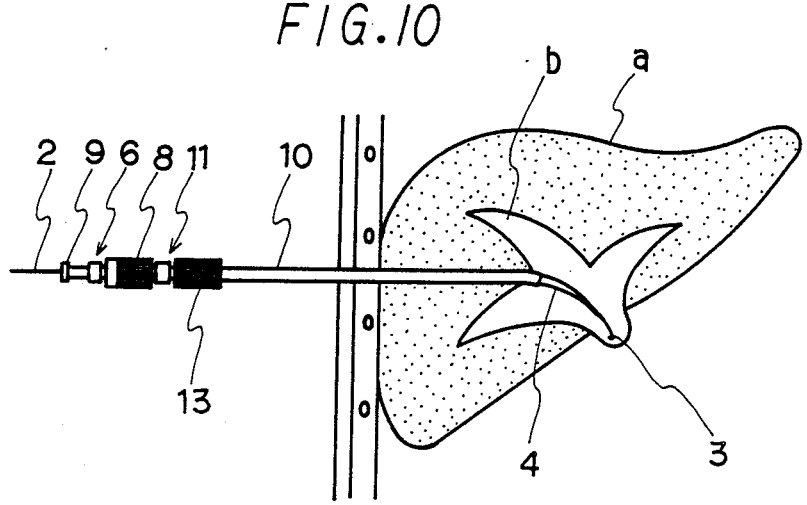
Figure 11:
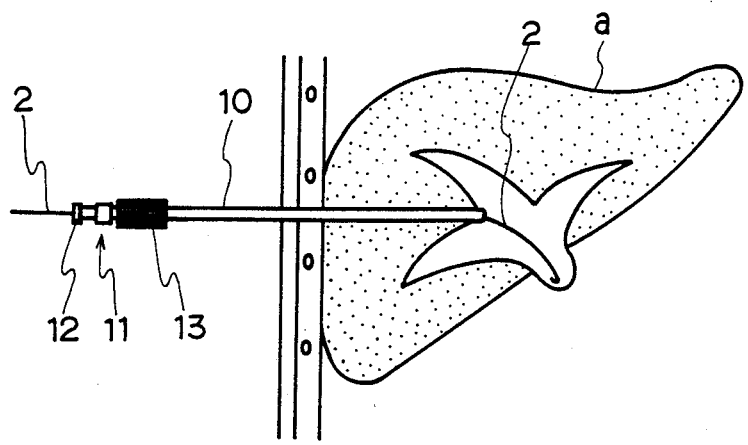

Next, an embodiment of the present invention is explained based on the accompanying drawings. FIGS. 1 to 6 show main elements of a drainage device of the present invention, and FIGS. 7 to 13 show a procedure of manual bile drainage with the use of a device of the present invention. In the above manual bile drainage, first of all, a puncture needle 1 having a diameter of 22G. is inserted into the liver a through a right chest wall. After confirming the puncture of the needle 1 into the bile duct in the liver by the suck of bile, as shown in FIG. 8, a flexible guide wire 2 having an outer diameter of 0.018 inch is inserted into the puncture needle 1 to a closed portion of the bile duct. The guide wire 2 is made of metal such as stainless steel and has a curled tip portion 3 as shown in FIG. 1. The guide wire 2 can be easily inserted into the puncture needle 1 by keeping the tip portion 3 straight and inserting the tip portion 3 into an opening at a proximal portion of the puncture needle 1. The tip portion 3 returns to its original curled shape by the elasticity thereof when it projects from an opening of the tip portion of the needle 1. Then the puncture needle 1 is pulled out as shown in FIG. 9 while the guide wire remains as it is.

FIG. 2 shows, a tube-like dilator 4. The dilator 4 is made of "Teflon" so as to be elastically bendable, and has an outer diameter of 7-french (1mm is 3 frenches). The dilator 4 has an inner diameter capable of covering an outer periphery of the guide wire 2. The outer diameter of a tip portion 5 of the dilator 4 is gradually reduced toward its end to be taper-shaped. It is preferable that a degree of taper of the tip portion is about one-tenth to one-fourth. When the degree of taper is larger than the above-mentioned range, an insertion of the dilator 4 into the liver becomes difficult. On the other hand, when the degree of taper is smaller than the above-mentioned range, a dilation of the abdominal cavity becomes difficult if the abdominal cavity is shallow. A fastening jack 6 made of synthetic resin is attached to a proximal portion of the dilator 4. The fastening jack 6 has a short tubular member 7 communicating with the inside of the dilator 4. A cap-nut-like fastening ring 8 is slidably and rotatably provided around an outer periphery of the tubular member 7. A flange 9 is integrally formed with the tubular member 7 at a tip portion thereof.

FIG. 3 shows a sheath 10 made of Teflon and having a thin wall. The sheath 10 is shorter than the dilator 4 and covers an outer periphery of the dilator 4. A fastening plug 11 is attached to a proximal portion of the sheath 10. A short tubular member 27 of the fastening plug 11 communicates with the inside of the sheath 10, and a flange 12 is integrally formed with the tubular member 27 at a tip thereof Numeral 13 is a screwed portion fixing the short tubular member 27 to an end of the sheath 10.

FIG. 4 shows a drainage tube 14 having an outer diameter of 7-french which is equal to that of the above-mentioned dilator 4. The drainage tube 14 comprises a tubular body made of synthetic resin wherein a steel mesh is embedded in a circumferential direction approximately between an inner wall and an outer wall. Though the drainage tube 14 is made thin to obtain a sufficient inner diameter, the drainage tube 14 has an improved mechanical strength due to the use of the steel mesh so that it does not easily deform by the externl force. A tip portion 15 between a tip of the drainage tube 14 and a portion about 5 cm from the tip does not contain a steel mesh and has a soft elasticity. The tip portion 15 has holes 15 and the tendency to curl.

Figure 5:
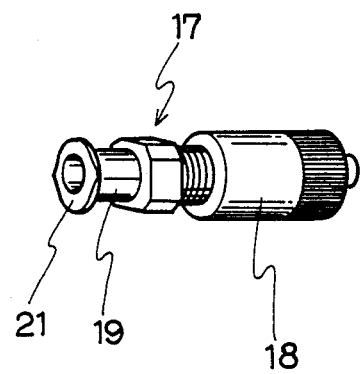
FIG. 5 is a perspective view of an embodiment of a universal fastening jack in the present invention.
Figure 6:
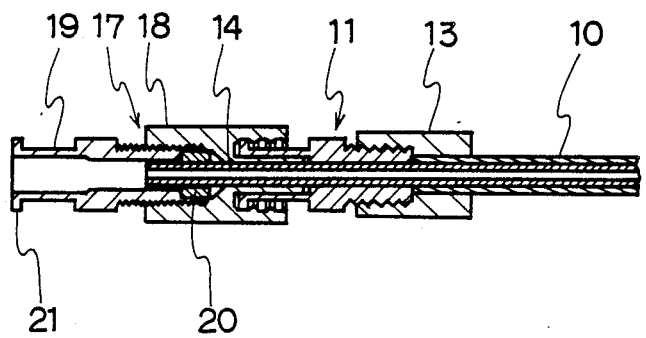
FIG. 6 is a longitudinal sectional view showing a state wherein the universal fastening jack is screwed to the fastening plug.
Figure 7:
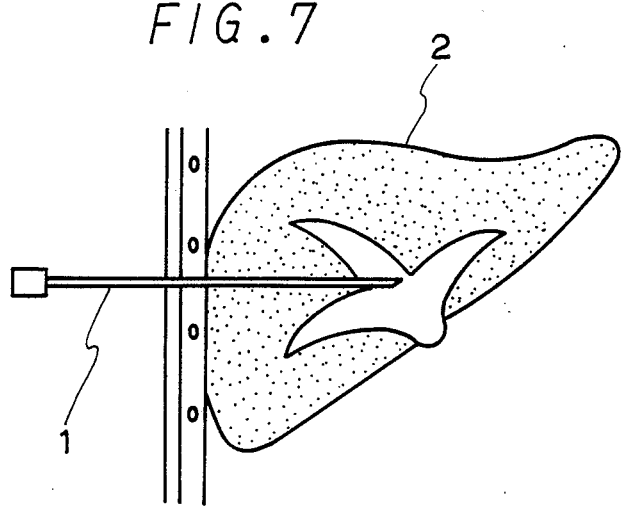
FIGS. 7 to 13 show sectional views of a liver showing a proceduce of manual bile drainage.

FIG. 5 shows a universal fastening jack 17, and FIG. 6 shows a section of the universal fastening jack 17. The universal fastening jack 17 comprises a cap-nut-like fastening ring 18 covering an outer periphery of the drainage tube and a short tubular member 19 capable of being screwed into the fastening ring 18. An elastic O-ring 20 is seated in the fastening ring 18. A flange 21 is integrally formed with the tubular member 19 at an end thereof.

When in use, the dilator 4 is inserted into the sheath 10 from a rear end of the sheath 10 and the fastening ring 8 of the fastening jack 6 is screwed to the flange 12 of the fastening plug 11, so as to put the sheath 10 on the outer periphery of the dilator 4. Thus, the dilator 4 and the sheath 10 are securely combined.

A rear end of the guide wire 2 inserted into the puncture needle 1 (as shown in FIG. 8) is put into the tip portion 5 of the dilator 4. Then the dilator 4 is inserted into the bile duct b along the guide wire 2 together with the sheath 10 which is put on the dilator 4 beforehand. Next the locking or connection between the sheath 10 and the dilator 4 is released and the sheath 10 is inserted into the bile duct b along the dilator 4. After the sheath 10 is inserted into the bile duct b, only the dilator 4 is pulled out while leaving the sheath 10 and the guide wire 2 in place (see FIG. 11).

Figure 12:
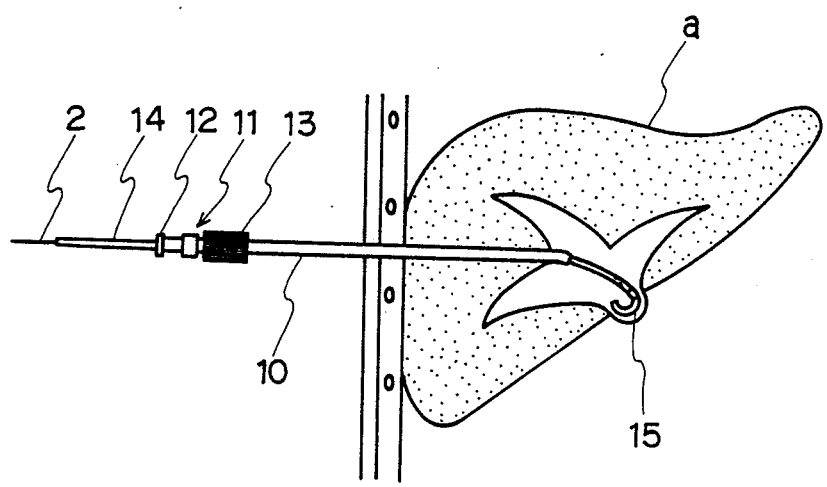

Then, the tip portion 15 of the drainage tube 14 is made straight and the rear end of the guide wire 2 is inserted into the tip portion 15. The drainage tube 14 is inserted into the sheath 10 through the flange 12. The tip portion 15 of the drainage tube 14 returns to its original curled shape when it projects from a tip portion of the sheath 10 as shown in FIG. 12.

Figure 13:
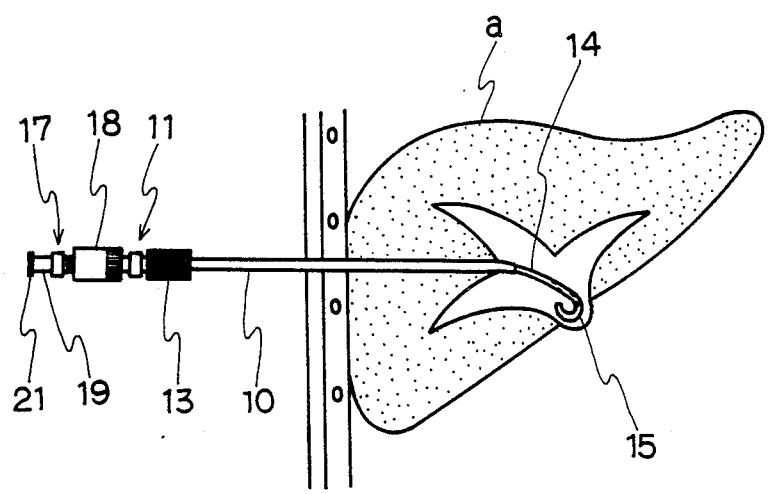

Thereafter, the guide wire 2 is pulled out, and the rear end portion of the drainage tube 14 is cut at a suitabe position. The cut end of the drainage tube 14 is inserted into the universal fastening jack 17 shown in FIG. 5 and the short tubular member 19 is screwed into the fastening ring 18, so that an O-ring 20 is compressed and pressed against an outer surface of the drainage tube 14, whereby the drainage tube 14 is fixed to the universal fastening jack 17. Then the fastening ring 18 is screwed to the flange 12 of the fastening plug 11 as shown in FIG. 13. Thus, the drainage tube 14 is fixed in the sheath 10, so that the operation of bile drainage becomes possible.

According to a drainage device of the present invention, the drainage becomes possible in one step with the use-of a puncture needle having a small diameter of 22 G. The method of using the drainage device is very easy.

The drainage tube in the present invention is made of synthetic resin and includes a mesh therein so that it has a large inner diameter in spite of a small outer diameter compared to a conventional drainage tube and has a sufficient strength. Accordingly, high drainage effect can be expected; that is, drainage efficiency can be improved. The drainage tube does not damage the mucous membrane of the bile duct since the tip portion of the drainage tube is made soft and elastic without a wire, and is curled.

By the insertion of the sheath which connects the chest wall and the liver as a kind of a bridge, the bending of the drainage tube on the surface of the liver can be prevented thereby effectively preventing the drainage tube from dislodging in the abdominal cavity. Further, by screwing the fastening plug 11 to the universal fastening jack 17, the drainage tube can be perfectly fixed in the sheath 10, and the leakage of bile and infection due to a clearance between the outer surface of the drainage tube 14 and the inner surface of the sheath 10 can be prevented.

Further, a pig-tail tube which gives a good drainage effect can be easily inserted into the body cavity because a sheath is used in the present invention. Without the use of sheath, the pig-tail tube cannot be easily inserted due to a bent tip portion thereof so that it damages tissue inside the body cavity.

Still further, the bending of a guide wire is prevented by the use of a dilator made of hard synthetic resin in the present invention, while in the conventional method, a guide wire sometimes bends when inserting a dull needle on which a catheter is put because the dull needle is made of metal and cannot follow the shape of the guide wire.

When the sheath 10 is not necessary, the sheath 10 might be pulled out after the insertion of the drainage tube 14 into the bile duct. The bile drainage can be carried out after the universal fastening jack 17 is attached to the rear end portion of the drainage tube 14.

Although the explanation is made based on the bile drainage in the embodiment explained above, the drainage device of the present invention can also be applied to percutaneous drainage such as cholecyst drainage, renal pelvis drainage and abscess drainage.

In summary, according to a drainage device of the prevent invention, the insertion of drainage tube is simplified and accordingly, the mannual drainage can be carried out in a short period of time. Further, the dislodgement of the drainage tube can be prevented so that the stability or accuracy of a drainage can be improved.

While the invention has been particularly shown and described in reference to preferred embodiments thereof, it will be understood by those skilled in the art that changes in form and details may be made therein without departing from the spirit and scope of the invention.

What is claimed is:

1. A drainage device for use in a body cavity comprising:
    a puncture needle;
    a flexible metallic guide wire insertable into said puncture needle;
    a tube-like dilator having a front end aperture for inserting therein said guide wire when said puncture needle has been withdrawn from said guide wire, said dilator being made of a synthetic resin and bendable, a front portion of said dilator having an outer diameter which gradually reduces toward a tip portion thereof;
    a fastening jack coupled to a back portion of said dilator;
    a sheath for covering the outer periphery of the dilator, said sheath having a length shorter than the length of said dilator;
    a fastening plug attached to a back portion of said sheath for liquid-tightly coupling with said fastening jack of said dilator;
    a drainage tube for inserting into said sheath, and said drainage tube having a front end aperture for inserting therein said guide wire for covering said guide wire when said fastening jack is detached from said fastening plug for withdrawing said dilator from said sheath, said drainage tube being made of synthetic resin, and said drainage tube having a tip portion which is curled, and a portion other than said curled portion which has wire imbedded therein; and
    a universal fastening jack removably attached to a back portion of said drainage tube for liquid-tightly coupling with said fastening plug of said sheath.

2. The drainage device as in claim 1, wherein said tip portion of said drainage tube has apertures for receiving liquid to be drained.

* * * * *